(12) United States Patent
Dimke

(10) Patent No.: US 6,211,389 B1
(45) Date of Patent: Apr. 3, 2001

(54) METHODS OF REDUCING THE CHLORIDE CONTENT OF EPOXY COMPOUNDS

(75) Inventor: Mark Thomas Dimke, Walnut, CA (US)

(73) Assignee: Dexter Corporation, Industry, CA (US)

( * ) Notice: Subject to any disclaimer, the term of this patent is extended or adjusted under 35 U.S.C. 154(b) by 0 days.

(21) Appl. No.: 09/578,785

(22) Filed: May 23, 2000

(51) Int. Cl.[7] ................. C07D 301/32; C07D 303/23
(52) U.S. Cl. ................. 549/542; 549/541; 549/555; 549/556; 549/558; 549/559; 549/560
(58) Field of Search .................... 549/542, 541, 549/555, 556, 558, 559, 560

(56) References Cited

U.S. PATENT DOCUMENTS

| | | | |
|---|---|---|---|
| 4,447,598 | 5/1984 | Caskey et al. | 528/489 |
| 4,485,221 | 11/1984 | Krueger et al. | 527/507 |
| 4,535,150 | 8/1985 | Hunter | 528/489 |
| 4,585,838 | 4/1986 | Wang et al. | 525/507 |
| 4,617,357 | 10/1986 | Pallie et al. | 525/506 |
| 4,668,807 | 5/1987 | Darbellay et al. | 549/542 |
| 4,684,701 | 8/1987 | Wang et al. | 525/507 |
| 4,785,061 | 11/1988 | Wang et al. | 525/507 |
| 4,924,013 | 5/1990 | Hunter | 549/514 |
| 5,098,965 | 3/1992 | Bauer et al. | 525/507 |
| 5,162,547 | * 11/1992 | Roth et al. | 549/516 |
| 5,342,903 | * 8/1994 | Wolleb et al. | 525/407 |

OTHER PUBLICATIONS

Ohsawa, et al., "Dissolving Metal Reduction by Crown Either—Hydrogenolysis of Alkyl Fluorides" *Tetrahedron Letter*22:(27) 2583–2586 (1981).

Nelsen and Kapp, "8,8'–Bibicyclo[3.3.1]octylidene Radical Cation" *Journal of American Chemical Society*, 108:(6) 1265–1270 (1986).

Bose and Mangiaracina, "Tris(3,6–Dioxaheptyl)Amine: A Superior Complexing Agent For Dissolving Metal Reactions" *Tetrahedron Letters*28:(22) 2503–2506 (1987).

* cited by examiner

*Primary Examiner*—Ba K. Trinh
(74) *Attorney, Agent, or Firm*—Gray Cary Ware & Freidenrich; Stephen E. Reiter

(57) ABSTRACT

In accordance with the present invention, methods have been developed for the reduction of the chloride content of epoxy compound starting materials. Invention methods comprise subjecting specifically defined combinations comprising an epoxy resin starting material and other components to conditions sufficient to produce a treated epoxy compound (i.e., an epoxy compound having a chloride content which is reduced relative to that of the epoxy resin starting material), and separating the treated epoxy compound from the combination. Other components contemplated for use in the practice of the present invention comprise, alternatively, mixtures of crown ether, organic solvent and suitable base; mixtures of crown ether-like solvent and suitable base; mixtures of aprotic solvents and hydrides (other than tin hydride); mixtures of nonhalogenated organic solvent and reducing metal; and the like. In accordance with a further aspect of the present invention, products (i.e., treated epoxy compounds, encapsulants and fillers) are provided which have been produced by the invention methods.

51 Claims, No Drawings

METHODS OF REDUCING THE CHLORIDE CONTENT OF EPOXY COMPOUNDS

FIELD OF THE INVENTION

The present invention relates generally to methods for reducing the chloride content of epoxy compound starting materials. Epoxy materials treated according to the invention are useful in a variety of applications, e.g., in the field of microelectronic devices. Thus, epoxy materials treated according to the invention are especially useful to formulate encapsulants and underfills for microelectronic devices.

BACKGROUND OF THE INVENTION

Microelectronic devices are useful in a variety of consumer and industrial applications. Microelectronic devices are prepared utilizing a variety of chemical formulations, e.g., encapsulants and/or underfills. A typical component of encapsulants and underfills is a compound having at least one epoxy reactive group. A common impurity of such epoxy-containing compounds is chloride. Unfortunately, chloride is known to corrode the wire bonds within microelectronic devices. Thus, a major problem associated with microelectronic devices is the tendency of certain residual impurities (e.g., chloride) within the microelectronic devices to decrease the reliability of the device by enhancing the corrosion of the wire bonds within the device, thereby increasing the risk of the device's failure.

There are only limited examples in the prior art of the use of chemical means to reduce the chloride content of epoxy-containing compounds. Thus, prior art methods of reducing the chloride content of epoxy-containing compounds utilize alkoxide/hydroxide bases in various organic solvents. However, these prior art methods suffer from a variety of deficiencies, e.g., high cost, high degree of complexity in setting up and running the reactions required to reduce the chloride content, insufficient chloride content reduction for chloride-sensitive end use applications, and the like.

Accordingly, there is a need in the art for new and better methods of reducing chloride content of epoxy compound starting materials. In addition, there is a need for epoxy compounds having reduced chloride content. Further, it would be highly desirable if such epoxy compound starting materials could be treated to reduce the chloride content thereof without suffering from increased viscosity.

BRIEF DESCRIPTION OF THE INVENTION

In accordance with the present invention, methods have been developed for the reduction of the chloride content of epoxy compound starting materials. Invention methods comprise subjecting specifically defined combinations comprising an epoxy resin starting material and other components to conditions sufficient to produce a treated epoxy compound (i.e., an epoxy compound having a chloride content which is reduced relative to that of the epoxy resin starting material), and separating the treated epoxy compound from the combination. Other components contemplated for use in the practice of the present invention comprise, alternatively, mixtures of crown ether, organic solvent and suitable base; mixtures of crown ether-like solvent and suitable base; mixtures of aprotic solvents and hydrides (other than tin hydride); mixtures of nonhalogenated organic solvent and reducing metal; and the like; as well as suitable combinations of any two or more thereof. Surprisingly, the treated epoxy compound separated from the combination contains substantially reduced chloride levels relative to the epoxy compound starting material.

In accordance with a further aspect of the present invention, products (i.e., treated epoxy compounds, encapsulants and fillers) are provided which have been produced by the invention methods. In addition, there are provided formulations made from treated epoxy compounds provided by invention methods. Surprisingly, the invention products contain substantially reduced chloride levels relative to products made without utilizing the invention methods.

The present invention provides many advantages over the art. For example, invention methods of reducing chloride content of epoxy compounds and compounds produced thereby are useful in preparing more reliable microelectronic devices. Invention methods provide purified epoxy compounds having reduced viscosity. Such formulations are useful in increasing the processibility of the formulation utilized in the preparation of microelectronic devices, thereby decreasing the cost of the prepared device and reducing the incidence of device failure. Other advantages of the present invention can be readily recognized by those of ordinary skill in the art.

DETAILED DESCRIPTION OF THE INVENTION

In accordance with the present invention, there are provided methods of reducing the chloride content of an epoxy compound starting material. In one aspect, invention methods accomplish this reduction utilizing organic solvent(s), crown ether(s) and suitable base(s). These invention methods comprise:

a) subjecting a combination comprising an epoxy compound starting material, an organic solvent, a crown ether, and a suitable base to conditions sufficient to produce a treated epoxy compound, wherein the chloride content of the treated epoxy compound is reduced by at least a predetermined value, relative to the chloride content of the epoxy compound starting material, and b) separating the treated epoxy compound from the combination.

As utilized herein, "chloride" includes ionic chlorine, hydrolyzable chlorine (e.g., C—Cl containing compounds; 1,2 chlorohydrin; and the like), and non-hydrolyzable chlorine (e.g., methyl chloride and the like). Chloride content is the amount of chloride present in, or associated with, an epoxy-containing compound (e.g., an epoxy compound starting material, portions thereof, a treated epoxy compound, and the like). The chloride content can readily be determined in a variety of ways, as are well known to those of skill in the art. Exemplary methods which can be employed for this purpose include X-ray fluorescence spectroscopy (XRF), infrared spectroscopy (IR), gas chromatography (GC), gas chromatography-mass spectroscopy (GCMS), mass spectroscopy (MS), atomic absorption (AA), inductively coupled plasma (ICP), and the like. Methodologies useful for measurement of chloride content are well documented and known to those of skill in the art. See, for example, ASTM D-18470 (for measuring amount of total chloride) and ASTM D-1726 (for measuring amount of hydrolyzable chlorides).

Epoxy compound starting materials contemplated for treatment in accordance with the present invention include epoxy resins and epoxy diluents. Epoxy resins include resins in liquid or solid form which have at least two epoxy groups and which are capable of cross linking (i.e., homo- or hetero-polymerizing) in a formulation useful as an encapsulant or an underfill for microelectronic devices. Epoxy resins may have a range of molecular weights, and specifically include low molecular weight epoxy resins, which are epoxy resins having a molecular weight of no greater than 500. Epoxy resins can have a variety of epoxy equivalent weights (EEW), including EEWs in the range from about 45 to about 500, in a preferred range from about 90 to about 230, or in a presently preferred range from about 125 to about 200. Exemplary epoxy resins contemplated for use in the practice of the present invention include resins typically having in the range of about 2 to about 6 glycidyl groups, with a preferred range of about 2 to about 4 glycidyl groups. Exemplary epoxy resins include resins of the general formulae:

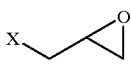

wherein
X=

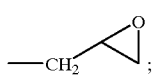

or

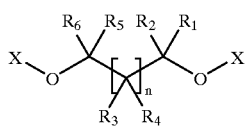

wherein:
X is as defined above,
each of $R_1$–$R_6$ is independently hydrogen, an alkyl, a substituted alkyl or a nonchloro-halogen, and
n=0 to 6; or

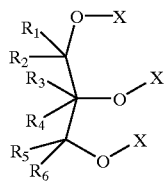

wherein:
X is as defined above, and
each of $R_1$–$R_6$ is independently hydrogen, a lower alkyl, a substituted lower alkyl, or a nonchloro-halogen; or

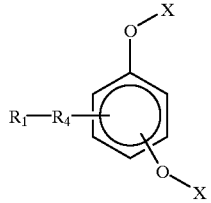

wherein:
X is as defined above, and
each of $R_1$–$R_4$ is independently hydrogen, an alkyl, a substituted alkyl, or a nonchloro-halogen; or

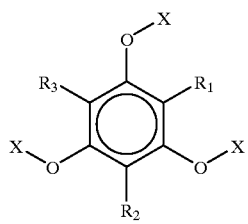

wherein:
X is as defined above, and
each of $R_1$–$R_3$ is independently hydrogen, an alkyl, a substituted alkyl, or a nonchloro-halogen; or

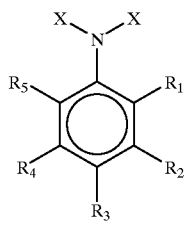

wherein:
X is as defined above, and
each of $R_1$–$R_5$ is independently hydrogen, an alkyl, a substituted alkyl, or a nonchloro-halogen; or

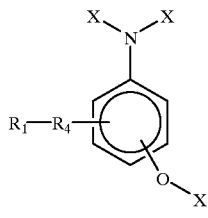

wherein:
X is as defined above, and
each of $R_1$–$R_4$ is independently hydrogen, an alkyl, a substituted alkyl, or a nonchloro-halogen; or

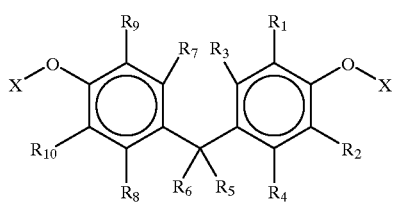

wherein:
X is as defined above, and
each of $R_1$–$R_{10}$ is independently hydrogen, an alkyl, a substituted alkyl or a nonchloro-halogen; or

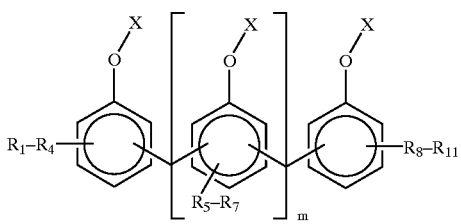

wherein:
X is as defined above,
each of $R_1$–$R_{11}$ is independently hydrogen, an alkyl, a substituted alkyl or a nonchloro-halogen, and
m=0 to 5; or

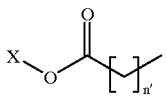

wherein:
X is as defined above, and
n'=4 to 20; or

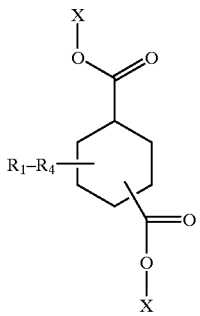

wherein:
X is as defined above, and
each of $R_1$–$R_4$ is independently hydrogen, an alkyl, a substituted alkyl or a nonchloro-halogen; or

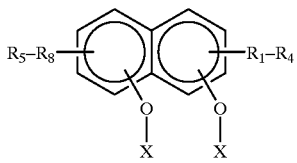

wherein:
X is as defined above, and
each of $R_1$–$R_4$ and $R_5$–$R_8$ is independently hydrogen, an alkyl, a substituted alkyl or a nonchloro-halogen,
with the proviso that when both —O—X groups are linked to the same carbon ring of the naphthalene molecule, the ring not having —O—X groups acquires one of the $R_n$ groups of the ring having both —O—X groups;
and the like; or suitable combinations of two or more thereof.

As utilized herein, "nonchloro-halogen" includes F, Br, I and At.

As utilized herein, "alkyl" includes acyclic, straight or branched chain radicals having in the range of about 1 up to about 20 carbon atoms, wherein all carbon atoms of the radical are linked by single bonds, the carbon atoms are fully saturated and have hydrogen radicals or hydrocarbon side chain radicals as their only other substituents, and one hydrogen radical is removed from the chain.

As utilized herein, "lower alkyl" refers to an alkyl having in the range of about 1 to about 6 carbon atoms.

As utilized herein, "substituted alkyl" refers to an alkyl wherein one or more of the hydrogen radical substituents has been replaced by another substituent such as hydroxy, alkoxy (of a lower alkyl), mercapto (of a lower alkyl), nonchloro-halogen, trifluoromethyl, cyano, nitro, amino, carboxyl, carbamate, sulfonyl, sulfonamide, and the like.

Specific examples of epoxy resins contemplated for use in the practice of the present invention include N,N-diglycidyl aniline, N,N-diglycidyl-4-glycidyloxyaniline, diglycidyl 1,2-cyclohexanedicarboxylate, diglycidyl 1,2,3,4-tetrahydrophthalate, bis(4-glycidyloxyphenyl)methane, 4,4'-isopropylidenediphenol diglycidyl ether, resorcinol diglycidyl ether, and the like, as well as suitable combinations of any two or more thereof.

Epoxy diluents contemplated for use in the practice of the present invention include liquid diluents which comprise at least one epoxy group and which have a viscosity which is sufficiently low to permit the liquid diluent to function as a viscosity reducer in a formulation useful as an encapsulant or underfill for microelectronic devices. Epoxy diluents include liquid diluents which are capable of cross linking (i.e., homo- or hetero-polymerizing) in a formulation useful as an underfill or an encapsulant for microelectronic devices. Epoxy diluents can have a variety of epoxy equivalent weights (EEW), including EEWs in the range from about 45 to about 250, in a preferred range from about 90 to about 250, or in a presently preferred range from about 100 to about 200. Exemplary epoxy diluents contemplated for use in the practice of the present invention include liquid diluents having in the range of about 1 to about 3 glycidyl groups, with a preferred range of about 1 to about 2 glycidyl groups. Exemplary epoxy diluents include liquid diluents of the general formulae:

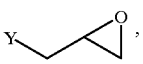

wherein

Y=

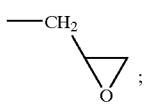

or

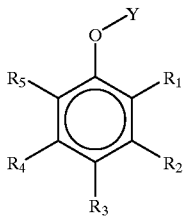

wherein:
Y is as defined above, and
each of $R_1$–$R_5$ is independently hydrogen, an alkyl, a substituted alkyl or a nonchloro-halogen; or

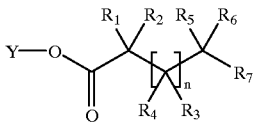

wherein:
Y is as defined above,
each of $R_1$–$R_7$ is independently hydrogen, an alkyl, a substituted alkyl or a nonchloro-halogen, and
n=0 to 20; or

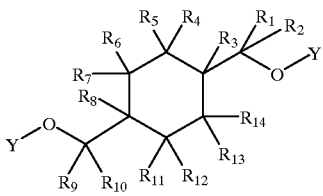

wherein:
Y is as defined above, and
each of $R_1$–$R_{14}$ is independently hydrogen, a lower alkyl, a substituted lower alkyl or a nonchloro-halogen; or

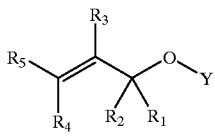

wherein:
Y is as defined above, and
each of $R_1$–$R_5$ is independently hydrogen, an alkyl, a substituted alkyl or a nonchloro-halogen; or

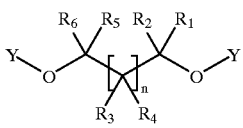

wherein:
Y is as defined above,
each of $R_1$–$R_6$ is independently hydrogen, an alkyl, a substituted alkyl or a nonchloro-halogen, and
n=0 to 6; or

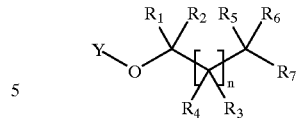

wherein:
Y is as defined above, and
each of $R_1$–$R_7$ is independently hydrogen, an alkyl, a substituted alkyl or a nonchloro-halogen, and
n=0 to 20; or

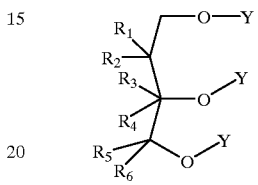

wherein:
Y is as defined above, and
each of $R_1$–$R_6$ is independently hydrogen, an alkyl, a substituted alkyl or a nonchloro-halogen; or

wherein:
Y is as defined above, and
R is an alkyl or a substituted alkyl; or
the like; or suitable combinations of two or more thereof.

Specific examples of epoxy diluents contemplated for use in the practice of the present invention include 1,4-butanediol diglycidyl ether; neopentyl glycol diglycidyl ether; 1,2-epoxy-3-phenoxypropane; benzyl glycidyl ether; glycidyl isopropyl ether; glycidyl isobutyl ether; glycidyl methyl ether; glycidyl 2-methylphenyl ether; glycidyl 4-methoxyphenyl ether; glycidyl 4-nonylphenyl ether; 1,4-cyclohexanedimethanol diglycidyl ether; 4-tert-butylphenyl glycidyl ether; butyl glycidyl ether; tert-butyl glycidyl ether; trimethylolpropane triglycidyl ether; allyl glycidyl ether; and the like; as well as suitable combinations of any two or more thereof.

Epoxy compound starting materials contemplated for use in the practice of the present invention also include glycidyl ethers of compounds selected from phenols, cresol formaldehyde, polyhydroxy phenols, polyaromatic phenols, aliphatic alcohols, polyglycols, aromatic amines, and the like, as well as suitable combinations of any two or more thereof.

Exemplary glycidyl ethers of phenols suitable for use as epoxy compound starting materials include phenyl glycidyl ethers, cresyl glycidyl ethers, nonylphenyl glycidyl ethers, and p-tert-butylphenyl glycidyl ethers, and the like, as well as suitable combinations of any two or more thereof. Exemplary glycidyl ethers of phenols also include diglycidyl ethers of: bisphenols (e.g., bisphenol A, bisphenol F, and the like), ethylidinebisphenol, dihydroxydiphenyl ether, N,N'-disalicylal-ethylenediamine, arin, bis(4-hydroxyphenyl) sulfone, bis(hydroxyphenyl)sulfide, 1,1-bis(hydroxyphenyl) cyclohexane, 9,19-bis(4-hydroxyphenyl)fluorene, 1,1,1-tris (hydroxyphenyl)ethane, trihydroxytritylmethane, 4,4'-(1-alpha-methylbenzylidene)bisphenol, 4,4'-(1,3-diethylethylene)diphenol, diethylstilbesterol, 4,4'- dihyroxybenzophenone, resorcinol, catechol, tetrahydroxydiphenyl sulfide, and the like, as well as suitable combinations of any two or more thereof.

Exemplary glycidyl ethers of fused ring polyaromatic phenols suitable for use as epoxy compound starting materials include glycidyl ethers of: dihydroxy naphthalene, 2,2'-dihydroxy-6,6'-dinaphthyl disulfide, 1,8,9-trihydroxyanthracene, and the like, as well as suitable combinations of any two or more thereof.

Exemplary glycidyl ethers of aliphatic alcohols suitable for use as epoxy compound starting materials include diglycidyl ethers of 1,4 butanediol, diglycidyl ethers of neopentyl glycol, diglycidyl ethers of cyclohexane dimethanol, trimethyol ethane triglycidyl ethers, trimethyol propane triglycidyl ethers, and the like, as well as suitable combinations of any two or more thereof.

Exemplary glycidyl ethers of polyglycols suitable for use as epoxy compound starting materials include Heloxy 84™:

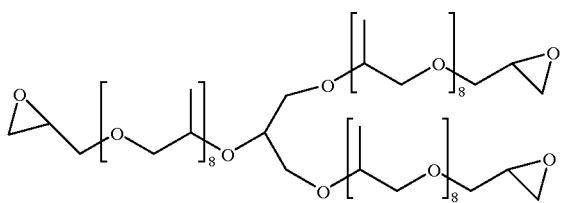

Heloxy 32™:

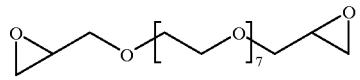

polyglycidyl ethers of castor oil, polyoxypropylene diglycidyl ethers, and the like, as well as suitable combinations of any two or more thereof.

Exemplary glycidyl ethers of aromatic amines suitable for use as epoxy compound starting materials include 4,4'-methylenebis(N,N-diglycidylaniline), bis-oxiranYlmethyl-(2,3,6-tribromo-phenyl)-amine, N,N'-diglycidyl-4-glycidyoxyamine, and the like.

Organic solvents contemplated for use in the practice of the present invention include all organic solvents which can function to solvate at least a part of the combination being subjected to conditions sufficient to produce a treated epoxy compound. Thus, in this aspect of the present invention (i.e., directed to methods of reducing the chloride content of an epoxy compound starting material utilizing organic solvent (s), crown ether(s) and suitable base(s)), exemplary organic solvents include halogenated solvents, hydrocarbon solvents, aromatic hydrocarbon solvents, ether solvents, cyclic ether solvents, alcohol solvents, ketone solvents, nitrile solvents, sulfoxide solvents, amide solvents, and the like, as well as suitable combinations of any two or more thereof.

Exemplary halogenated solvents suitable for use in the practice of the present invention include carbon tetrachloride, methylene chloride, chloroform, tetrachloroethylene, chlorobenzene, bis(2-chloroethyl)ether, chloromethyl ethyl ether, chloromethyl methyl ether, 2-chloroethyl ethyl ether, 2-chloroethyl propyl ether, 2-chloroethyl methyl ether, and the like, as well as suitable combinations of any two or more thereof.

Exemplary hydrocarbon solvents suitable for use in the practice of the present invention include pentane, hexane, cyclohexane, heptane, octane, decahydronaphthalene, petroleum ethers, ligroine, and the like, as well as suitable combinations of any two or more thereof.

Exemplary aromatic hydrocarbon solvents suitable for use in the practice of the present invention include benzene, naphthalene, toluene, xylene, ethyl benzene, cumene (iso-propyl benzene) mesitylene (trimethyl benzene), ethyl toluene, butyl benzene, cymene (iso-propyl toluene), diethylbenzene, iso-butyl benzene, tetramethyl benzene, sec-butyl benzene, tert-butyl benzene, and the like, as well as suitable combinations of any two or more thereof.

Exemplary ether solvents suitable for use in the practice of the present invention include diethyl ether, ethyl propyl ether, dipropyl ether, disopropyl ether, dibutyl ether, methyl t-butyl ether, glyme, diglyme, benzyl methyl ether, isochroman, 2-phenylethyl methyl ether, n-butyl ethyl ether, 1,2-diethoxyethane, sec-butyl ether, diisobutyl ether, ethyl n-propyl ether, ethyl isopropyl ether, n-hexyl methyl ether, n-butyl methyl ether, methyl n-propyl ether, and the like, as well as suitable combinations of any two or more thereof.

Exemplary cyclic ether solvents suitable for use in the practice of the present invention include tetrahydrofuran, dioxane, tetrahydropyran, 4 methyl-1,3-dioxane, 4-phenyl-1,3-dioxane, 1,3-dioxolane, 2-methyl-1,3-dioxolane, 1,4-dioxane, 1,3-dioxane, 2,5-dimethoxytetrahydrofuran, 2,5-dimethoxy-2,5-dihydrofuran, and the like, as well as suitable combinations of any two or more thereof.

Exemplary alcohol solvents suitable for use in the practice of the present invention include methanol, ethanol, 1-propanol, 2-propanol, 1-butanol, 2-butanol, 2-methyl-1-propanol (i.e., iso-butanol), 2-methyl-2-propanol (i.e., tert-butanol), 1-pentanol, 2-pentanol, 3-pentanol, 2,2-dimethyl-1-propanol, 1-hexanol, cyclopentanol, 3-methyl-1-butanol, 3-methyl-2-butanol, 2-methyl-1-butanol, 2,2-dimethyl-1-propanol, 3-hexanol, 2-hexanol, 4-methyl-2-pentanol, 2-methyl-1-pentanol, 2-ethylbutanol, 2,4-dimethyl-3-pentanol, 3-heptanol, 4-heptanol, 2-heptanol, 1-heptanol, 2-ethyl-1-hexanol, 2,6-dimethyl-4-heptanol, 2-methylcyclohexanol, 3-methylcyclohexanol, 4-methylcyclohexanol, and the like, as well as suitable combinations of any two or more thereof.

Glycol solvents may also be used provided that they are removed by suitable means, e.g., aqueous extraction, or the like. Exemplary glycol solvents suitable for use in the practice of the present invention include ethylene glycol, 1,3-propanediol, 1,2-propanediol, 1,3-butanediol, 1,4-butanediol, 2,3-butanediol, 3-methyl-1,5-pentanediol, 1,4-cyclohexanediol, 1,3-cyclohexanediol, 1,4-cyclohexanedimethanol, dipropylene glycol, and the like, as well as suitable combinations of any two or more thereof.

Alcohol ether solvents may also be employed. Exemplary alcohol ether solvents suitable for use in the practice of the present invention include 1-methoxy-2-propanol, 2-methoxyethanol, 2-ethoxyethanol, 1-methoxy-2-butanol, ethylene glycol monoisopropyl ether, 1-ethoxy-2-propanol, 3-methoxy-1-butanol, ethylene glycol monoisobutyl ether, ethylene glycol mono-n-butyl ether, 3-methoxy-3-methylbutanol, ethylene glycol momo-tert-butyl ether, and the like, as well as suitable combinations of any two or more thereof.

Exemplary ketone solvents suitable for use in the practice of the present invention include acetone, methylethyl ketone, methyl iso-butyl ketone, cyclohexanone, isopropyl methyl ketone, 2-pentanone, 3-pentanone, 3-hexanone, diisopropyl ketone, 2-hexanone, cyclopentanone, 4-heptanone, iso-amyl methyl ketone, 3-heptanone, 2-heptanone, 4-methoxy-4-methyl-2-pentanone, 5-methyl- 3-heptanone, 2-methylcyclohexanone, diisobutyl ketone, 5-methyl-2-octanone, 3-methylcyclohexanone, 2-cyclohexen-1-one, 4-methylcyclohexanone, cycloheptanone, 4-tert-butylcyclohexanone, isophorone, benzyl acetone, and the like, as well as suitable combinations of any two or more thereof.

Exemplary nitrile solvents suitable for use in the practice of the present invention include acetonitrile, acrylonitrile, trichloroacetonitrile, propionitrile, pivalonitrile, isobutyronitrile, n-butyronitrile, methoxyacetonitrile, 2-methylbutyronitrile, isovaleronitrile, N-valeronitrile, n-capronitrile, 3-methoxypropionitrile, 3-ethoxypropionitrile, 3,3'-oxydipropionitrile, n-heptanenitrile, glycolonitrile, benzonitrile, ethylene cyanohydrin, succinonitrile, acetone cyanohydrin, 3-n-butoxypropionitrile, and the like, as well as suitable combinations of any two or more thereof.

Exemplary sulfoxide solvents suitable for use in the practice of the present invention include dimethyl sulfoxide, di-n-butyl sulfoxide, tetramethylene sulfoxide, methyl phenyl sulfoxide, and the like, as well as suitable combinations of any two or more thereof.

Exemplary amide solvents suitable for use in the practice of the present invention include dimethyl formamide, dimethyl acetamide, acylamide, 2-acetamidoethanol, N,N-dimethyl-m-toluamide, trifluoroacetamide, N,N-dimethylacetamide, N,N-diethyldodecanamide, epsilon-caprolactam, N,N-diethylacetamide, N-tert-butylformamide, formamide, pivalamide, N-butyramide, N,N-dimethylacetoacetamide, N-methyl formamide, N,N-diethylformamide, N-formylethylamine, acetamide, N,N-diisopropylformamide, 1-formylpiperidine, N-methylformanilide, and the like, as well as suitable combinations of any two or more thereof.

Crown ethers contemplated for use in the practice of the present invention include all crown ethers which can function to assist in the reduction of the chloride content of an epoxy compound starting material as part of the combination being treated according to the invention. Exemplary crown ethers include benzo-15-crown-5; benzo-18-crown-6; 12-crown-4; 15-crown-5; 18-crown-6; cyclohexano-15-crown-5; 4',4"(5")-ditert-butyldibenzo-18-crown-6; 4',4" (5")-ditert-butyldicyclohexano-18-crown-6; dicyclohexano-18-crown-6; dicyclohexano-24-crown-8; 4'-aminobenzo-15-crown-5; 4'-aminobenzo-18-crown-6; 2-(aminomethyl)-15-crown-5; 2-(aminomethyl)-18-crown-6; 4'-amino-5'-nitrobenzo-15-crown-5; 1-aza-12-crown-4; 1-aza-15-crown-5; 1-aza-18-crown-6; benzo-12-crown-4; benzo-15-crown-5; benzo-18-crown-6; bis((benzo-15-crown-5)-15-ylmethyl)pimelate; 4-bromobenzo-18-crown-6; (+)-(18-crown-6)-2,3,11,12-tetra-carboxylic acid; dibenzo-18-crown-6; dibenzo-24-crown-8; dibenzo-30-crown-10; ar-ar'-di-tert-butyldibenzo-18-crown-6; 4'-formylbenzo-15-crown-5; 2-(hydroxymethyl)-12-crown-4; 2-(hydroxymethyl)-15-crown-5; 2-(hydroxymethyl)-18-crown-6; 4'-nitrobenzo-15-crown-5; poly-[(dibenzo-18-crown-6)-co-formaldehyde]; 1,1-dimethylsila-11-crown-4; 1,1-dimethylsila-14-crown-5; 1,1-dimethylsila-17-crown-5; cyclam; 1,4,10,13-tetrathia-7,16-diazacyclooctadecane; porphines; and the like; as well as suitable combinations of any two or more thereof.

Suitable bases contemplated for use in the practice of the present invention include all bases which can function to assist in the reduction of the chloride content of an epoxy compound starting material being treated according to the invention. Exemplary bases include alkoxides or hydroxides, carbonates, bicarbonates, phosphates, and the like, as well as suitable combinations of any two or more thereof.

Exemplary alkoxides or hydroxides suitable for use in the practice of the present invention include sodium hydroxide, potassium hydroxide, lithium hydroxide, rubidium hydroxide, cesium hydroxide, francium hydroxide, beryllium hydroxide, magnesium hydroxide, calcium hydroxide, strontium hydroxide, barium hydroxide, radium hydroxide, lithium methoxide, lithium ethoxide, lithium propoxide, lithium iso-propoxide, lithium butoxide, lithium iso-butoxide, lithium sec-butoxide, lithium tert-butoxide, sodium methoxide, sodium ethoxide, sodium propoxide, sodium iso-propoxide, sodium butoxide, sodium iso-butoxide, sodium sec-butoxide, sodium tert-butoxide, potassium methoxide, potassium ethoxide, potassium propoxide, potassium iso-propoxide, potassium butoxide, potassium iso-butoxide, potassium sec-butoxide, potassium tert-butoxide, lithium carbonate, lithium bicarbonate, sodium carbonate, sodium bicarbonate, potassium carbonate, potassium bicarbonate, and the like, as well as suitable combination of any two or more thereof.

Exemplary carbonates suitable for use in the practice of the present invention include sodium hydrogen carbonate, potassium hydrogen carbonate, lithium carbonate, and the like, as well as suitable combinations of any two or more thereof.

Exemplary bicarbonates suitable for use in the practice of the present invention include sodium bicarbonate, potassium bicarbonate, lithium bicarbonate, cesium bicarbonate, ammonium bicarbonate, and the like, as well as suitable combinations of any two or more thereof.

Exemplary phosphates suitable for use in the practice of the present invention include sodium phosphate, potassium phosphate, lithium phosphate, ammonium phosphate, and the like, as well as suitable combinations of any two or more thereof.

Conditions sufficient to produce a treated epoxy compound according to the present invention include temperature, pressure, contact time, and the like, as well as suitable combinations of any two or more thereof, which are effective to permit and/or enhance the reduction of the chloride content of the epoxy compound starting material found in the combination. Thus, in one aspect, conditions sufficient to produce said treated epoxy compound commonly include subjecting said combination to heat/cold so as to generate a temperature in the range from about −78° C. to about 250° C., in a preferred range from about 10° C. to about 150° C., or in a presently preferred range from about 25° C. to about 120° C. Treated epoxy compound is typically produced by subjecting said combination to suitable temperature (as set forth above), at any suitable pressure, i.e., at a pressure in the range from about 5 torr to about 300,000 torr, in a preferred range from about 400 torr to about 1,000 torr, or in a presently preferred range from about 740 torr to about 780 torr.

Commonly, combinations utilized in the practice of the present invention are subjected to conditions sufficient to produce said treated epoxy compound starting material for a contact time in the range from about 0.1 to about 168 hours, preferably in the range from about 0.5 to about 96 hours, and most preferably in the range from about 1 to about 24 hours.

The predetermined value by which the chloride content of the epoxy compound starting material is reduced can be expressed in a variety of ways. For example, this predetermined value can be expressed as a relative reduction, an absolute reduction, reduction below a target level, or the like.

As a relative reduction, this predetermined reduction is generally a percentage value (i.e., less than 100%) of the chloride content of the epoxy compound starting material, and is selected from a range of such values. Typically, the low end point of this predetermined reduction range is greater than or equal to about 1%. Another way of expressing acceptable values for the low end point of this predetermined reduction range is as any integer percentage value in the range from about 1% to about 95%. Exemplary low end points of this predetermined reduction range include 25%, 50%, 70%, 90%, and 95%. The corresponding upper end point of this predetermined reduction range is commonly less than or equal to about 99%. Another way of expressing acceptable values for this corresponding upper end point of this predetermined reduction range is as any integer percentage value which is greater than the low end point of this predetermined reduction range and which is in the range from about 5% to about 99%. Exemplary upper end points of this predetermined reduction range include 50%, 75%, 90%, 95%, and 99%. When selected from such specifically defined ranges, exemplary predetermined values by which the chloride content is reduced include 25%, 50%, 70%, and 90% of the chloride content of the epoxy compound starting material.

Alternatively, the target level of chloride content of the treated epoxy material can be expressed in parts per million (ppm). Thus, in one embodiment the chloride content of the treated epoxy is reduced to about 10,000 ppm or less. In another embodiment, the chloride content of the treated epoxy is reduced to about 5,000 ppm or less. In still another embodiment, the chloride content of the treated epoxy is in the range of about 500 ppm up to about 2,000 ppm. In yet another embodiment, the chloride content of the treated epoxy is reduced to below about 1000 ppm; while in further embodiments, the chloride content of the treated epoxy is reduced to below about 500 ppm, 200 ppm or 100 ppm.

As readily recognized by those of skill in the art, the predetermined value by which the chloride content is reduced, relative to the chloride content of the epoxy compound starting material, may vary depending on a variety of factors. These factors include the initial chloride content of the epoxy compound starting material, the desired chloride reduction in the treated epoxy compound, the boiling point of the epoxy compound starting material, the number of glycidyl groups of the epoxy compound starting material, the molecular weight of the epoxy compound starting material, the presence of other organic functionality(ies) on the epoxy compound starting material, the desired yield of treated epoxy compound, and the like.

Typically, the components of the combination utilized in the aspect of the present invention directed to methods of reducing the chloride content of an epoxy compound starting material utilizing organic solvent(s), crown ether(s), and suitable base(s) can be present in varying amounts.

The amount of epoxy compound starting material and organic solvent present in this combination is generally measured as a wt-wt % (compared to weight of the combination). Commonly, the combination utilized in that aspect of the present invention directed to methods of reducing the chloride content of an epoxy compound starting material utilizing organic solvent(s), crown ether(s), and suitable base(s) comprises epoxy compound starting material in an amount from about 1 wt-wt % to about 75 wt-wt %, and preferably in an amount from about 10 wt-wt % to about 30 wt-wt %. Typically, this combination further comprises organic solvent present in an amount from about 25 wt-wt % to about 98 wt-wt %, and preferably in an amount from about 70 wt-wt % to about 90 wt-wt %.

As readily recognized by those of skill in the art, the amount of crown ether and base present in this combination can be measured in a variety of ways (e.g., wt-wt % (compared to weight of the combination), mole equivalents when compared to undesirable chloride content, and the like). Thus, this combination can further comprise crown ether in an amount from about 0.00001 wt-wt % to about 20 wt-wt %. Alternatively, this combination can further comprise crown ether in an amount from about 0.1 to about 20 mole equivalents per mole equivalent of undesirable chloride content, and preferably in an amount from about 1 to about 5 mole equivalents per mole equivalent of undesirable chloride content. This combination can also comprise base in an amount from about 0.01 wt-wt % to about 10 wt-wt %. Alternatively, this combination can also comprise base in an amount from about 0.1 to about 20 mole equivalents per mole equivalent of undesirable chloride content, and preferably in an amount from about 1 to about 5 mole equivalents per mole equivalent of undesirable chloride content.

As utilized herein, the term "undesirable chloride content" includes the chloride content which is desired to be removed from the epoxy compound starting material. The mole equivalent of undesirable chloride content can be readily measured, prior to subjecting the combination to conditions sufficient to produce a treated epoxy compound, by means known to those of skill in the art, including, for example, X-ray fluorescence (XRF), and the like.

The separation of the treated epoxy compound from the combination utilized in the aspect of the present invention directed to methods of reducing the chloride content of an epoxy compound starting material utilizing organic solvent (s), crown ether(s) and suitable base(s) can be accomplished in a variety of ways, as recognized by those of skill in the art. Exemplary separation methodologies include organic/water biphasic extraction, followed by drying the organic phase over a suitable drying agent (such as $MgSO_4$, or the like), followed by Kugelrohr distillation, or like methods. Optionally, the treated epoxy resin is more effectively separated from the combination by subjecting the combination and/or extracts from the combination to flash distillation (for small scale productions, utilizing, for example, a Kugelrohr distillation apparatus), or wiped film still distillation (for large scale productions), or the like.

In another aspect, invention methods accomplish the reduction of the chloride content of an epoxy compound starting material by utilizing crown ether-like solvent(s) and suitable base(s). The se invention methods comprise:

a) subjecting a combination comprising an epoxy compound starting material, a crown ether-like solvent, and a suitable base to conditions sufficient to produce a treated epoxy compound, wherein the chloride content of the treated epoxy compound is reduced by at least a predetermined value, relative to the chloride content of the epoxy compound starting material, and b) separating the treated epoxy compound from the combination.

Crown ether-like solvents contemplated for use in the present invention include 1,2-dimethoxy ethane, bis(2-methoxyethyl)ether, 1,2-diethoxyethane, 1,2-bis(2-methoxyethoxy)ethane, 2-(2-methoxyethoxy)ethanol, Bis (2-ethoxyethyl)ether, polyethylene glycols having an average molecular weight in the range from about 200 to about 10,000, and the like, as well as suitable combinations of any two or more thereof.

Suitable bases contemplated for use in this embodiment of the present invention include all bases which can function to assist in the reduction of the chloride content of an epoxy compound starting material being treated according to the invention. Exemplary bases include any of the alkoxides or hydroxides, carbonates, bicarbonates, phosphates, and the like, as well as suitable combinations of any two or more thereof described hereinabove.

By this embodiment of the present invention, chloride reduction can be achieved to the same magnitude as referred to hereinabove, employing conditions comparable to those set forth hereinabove.

Typically, the components of the combination utilized in the aspect of the present invention directed to methods of reducing the chloride content of an epoxy compound starting material utilizing crown ether-like solvent(s) and suitable base(s) can be present in varying amounts.

The amount of epoxy compound starting material present in this combination is generally measured as a wt-wt % (compared to weight of the combination). Commonly, the combination utilized in the aspect of the present invention directed to methods of reducing the chloride content of an epoxy compound starting material utilizing crown ether-like solvent(s) and suitable base(s) comprises epoxy compound starting material present in an amount from about 1 wt-wt % to about 75 wt-wt %, and preferably in an amount from about 10 wt-wt % to about 30 wt-wt %.

The amount of crown ether-like solvent and suitable base present in this combination can be measured in a variety of ways (e.g., wt-wt % (compared to weight of the combination), mole equivalents when compared to undesirable chloride content, and the like), as readily recognized by those of skill in the art. Thus, this combination comprises crown ether-like solvent in an amount from about 50 wt-wt % to about 98 wt-wt %, and preferably in an amount from about 70 wt-wt % to about to about 90 wt-wt %. Alternatively, this combination comprises crown ether-like solvent present in an amount from about 0.1 to about 20 mole equivalents per mole equivalent of undesirable chloride content, and preferably in an amount from about 1 to about 5 mole equivalents per mole equivalent of undesirable chloride content. This combination also comprises suitable base in an amount from about 0.01 wt-wt % to about 10 wt-wt %, and preferably in an amount from about 0.02 wt-wt % to about 0.2 wt-wt %. Alternatively, this combination comprises suitable base present in an amount from about 0.1 to about 20 mole equivalents per mole equivalent of undesirable chloride content, and preferably in an amount from about 1 to about 5 mole equivalents per mole equivalent of undesirable chloride content.

Optionally, the combination utilized in accordance with this aspect of the present invention can further comprise a crown ether. Suitable crown ethers for use in the practice of this embodiment of the present invention include those described herein, and the like.

In another aspect, invention methods accomplish the reduction of the chloride content of an epoxy compound starting material by utilizing aprotic solvent(s) and hydride(s) other than tin hydride. These invention methods comprise:

a) subjecting a combination comprising an epoxy compound starting material, an aprotic solvent, and a hydride other than tin hydride to conditions sufficient to produce a treated epoxy compound, wherein the chloride content of the treated epoxy compound is reduced by at least a predetermined value, relative to the chloride content of the epoxy compound starting material, and b) separating the treated epoxy compound from the combination.

This method of treatment is more mild, yet produces a significant reduction of chloride content, usually competitive with that achieved using other methods described herein. Thus, treatment of chloride-containing epoxies according to this embodiment of the present invention can result in significant reductions of chloride content, typically down to about 5,000 to 10,000 ppm. In another aspect, the chloride content of the treated epoxy is reduced down to the range of about 2,000 ppm to about 5,000 ppm. In still another aspect of this embodiment, the chloride content of the treated epoxy is reduced down to the range of about 1,000 ppm to about 2,000 ppm. In most cases, 50% or greater reduction in chloride content can be achieved.

Typically, the components of the combination utilized in this aspect of the present invention (utilizing aprotic solvent (s) and hydride(s)) can be present in varying amounts. The amount of epoxy compound starting material present in this combination is generally measured as a wt-wt % (compared to weight of the combination). Commonly, the combination utilized in this aspect of the present invention comprises epoxy compound starting material in an amount from about 1 wt-wt % to about 70 wt-wt %, and preferably in an amount from about 10 wt-wt % to about 30 wt-wt %.

Similarly, the amount of aprotic solvent and hydride present in this combination can be measured in a variety of ways (e.g., wt-wt % (compared to weight of the combination), mole equivalents when compared to undesirable chloride content, and the like). Thus, this combination typically comprises aprotic solvent in an amount from about 30 wt-wt % to about 99 wt-wt %, and preferably in an amount from about 70 wt-wt % to about 90 wt-wt %. Alternatively, this combination comprises aprotic solvent in an amount from about 10 to about 5,000 mole equivalents per mole equivalent of undesirable chloride content, and preferably in an amount from about 50 to about 500 mole equivalents per mole equivalent of undesirable chloride content. This combination also typically comprises hydride in an amount from about 0.00001 wt-wt % to about 20 wt-wt %, and preferably in an amount from about 1 wt-wt % to about 10 wt-wt %. Alternatively, this combination also comprises hydride in an amount from about 0.1 to about 25 mole equivalents per mole equivalent of undesirable chloride content, and preferably in an amount from about 1 to about 5 mole equivalents per mole equivalent of undesirable chloride content.

Conditions sufficient to produce a treated epoxy compound utilized in accordance with the aspect of the present invention directed to methods of reducing the chloride content of an epoxy compound starting material utilizing aprotic solvent(s) and hydride(s) other than tin hydride further comprise heating and stirring the combination at a predetermined elevated temperature for a predetermined time sufficient to produce the treated epoxy compound. Thus, in this aspect of the invention, conditions sufficient to produce the treated epoxy compound commonly include subjecting said combination to heat/cold so as to generate a temperature in the range from about −78° C. to about 125° C., in a preferred range from about 0° C. to about 70° C., or in a presently preferred range from about 15° C. to about 40° C. In an additional aspect, conditions sufficient to produce said treated epoxy compound typically include subjecting said combination to a pressure in the range of from about 5 torr to about 300,000 torr, in a preferred range from about 400 torr to about 1,000 torr, or in presently preferred range from about 740 torr to about 780 torr.

Commonly, combinations utilized in the practice of the present invention are subjected to conditions sufficient to produce said treated epoxy compound starting material for a contact time in the range from about 0.1 to about 168 hours, preferably from about 0.5 to about 96 hours, and most preferably in the range from about 1 to about 24 hours.

The separation of the treated epoxy compound from the combination utilized in the aspect of the present invention (utilizing aprotic solvent(s) and hydride(s) other than tin hydride) can be accomplished by a variety of means, as recognized by those of skill in the art. Exemplary separation methodologies include biphasic extraction, dual distillation, chromatography, and the like, and suitable combinations of two or more thereof.

Epoxy compound starting materials commonly preferred for use in the practice of this aspect of the invention include heat sensitive epoxy compound starting materials which cannot be readily distilled without substantial decomposition. Examples of such heat sensitive epoxy compound starting materials are polyoxypropylene diglycidyl ether resin, and the like.

Aprotic solvents contemplated for use in the practice of the present invention include all organic solvents which are aprotic and which can function to solvate at least a part of the combination being subjected to conditions sufficient to produce a treated epoxy compound. Thus, in this aspect of the present invention (i.e., directed to methods of reducing the chloride content of an epoxy compound starting material utilizing aprotic solvent(s) and hydride(s) other than tin hydride), exemplary aprotic solvents include halogenated solvents, hydrocarbon solvents, aromatic hydrocarbon solvents, ether solvents, cyclic ether solvents, ketone solvents, nitrile solvents, sulfoxide solvents, amide solvents, other polar aprotic solvents, and the like, as well as suitable combinations of any two or more thereof.

Hydrides contemplated for use in the practice of the present invention include metal hydrides from the Group 1 elements, metal hydrides from the Group 2 elements, and the like, as well as suitable combinations of any two or more thereof, and exclude tin hydride. Exemplary hydrides include lithium hydride, sodium hydride, potassium hydride, rubidium hydride, cesium hydride, francium hydride, beryllium hydride, magnesium hydride, calcium hydride, strontium hydride, barium hydride, radium hydride, and the like, as well as suitable combinations of any two or more thereof.

In another aspect, invention methods accomplish the reduction of the chloride content of an epoxy compound starting material by utilizing nonhalogenated organic solvent(s) and reducing metal(s). These invention methods comprise:
  a) subjecting a combination comprising an epoxy compound starting material, a nonhalogenated organic solvent, and a reducing metal to conditions sufficient to produce a treated epoxy compound, wherein the chloride content of the treated epoxy compound is reduced by at least a predetermined value, relative to the chloride content of the epoxy compound starting material; and
  b) separating the treated epoxy compound from the combination.

The chloride reduction attainable with the utilization of nonhalogenated organic solvent(s) and reducing metal(s) is comparable to that attainable with invention methods utilizing crown ethers, as described hereinabove.

Conditions sufficient to produce a treated epoxy compound utilized in accordance with the aspect of the present invention directed to methods of reducing the chloride content of an epoxy compound starting material utilizing nonhalogenated organic solvent(s) and reducing metal(s) further comprise heating and stirring the combination at a predetermined elevated temperature for a predetermined time sufficient to produce the treated epoxy compound. Thus, in this aspect of the invention, conditions sufficient to produce said treated epoxy compound commonly include subjecting said combination to heat/cold so as to generate a temperature in the range from about −78° C. to about 250° C., in a preferred range from about 10° C. to about 150° C., or in a presently preferred range from about 25° C. to about 120° C. Conditions sufficient to produce said treated epoxy compound typically include subjecting said combination to a pressure in the range from about 5 torr to about 300,000 torr, in a preferred range from about 400 torr to about 1,000 torr, or in a presently preferred range from about 740 torr to about 780 torr.

Commonly, combinations utilized in the practice of the present invention are subjected to conditions sufficient to produce said treated epoxy compound starting material for a contact time in the range from about 0.1 to about 196 hours, preferably from about 6 to about 100 hours, and most preferably in the range from about 12 to about 72 hours.

Nonhalogenated organic solvents contemplated for use in this aspect of the present invention include all organic solvents which do not react with reducing metal(s) and which can function to solvate at least a part of the combination being subjected to conditions sufficient to produce a treated epoxy compound. Thus, in this aspect of the present invention (i.e., directed to methods of reducing the chloride content of an epoxy compound starting material utilizing nonhalogenated organic solvent(s) and reducing metal(s)), exemplary nonhalogenated organic solvents include hydrocarbon solvents, aromatic hydrocarbon solvents, ether solvents, cyclic ether solvents, alcohol solvents, ketone solvents, nitrile solvents, sulfoxide solvents, amide solvents, and the like, as well as suitable combinations of any two or more thereof.

Reducing metals contemplated for use in the practice of the present invention include Group 1 metals, Group 2 metals, transition metals, lanthanides, actinides, and the like, as well as suitable combinations of any two or more thereof. Exemplary reducing metals include lithium, sodium, potassium, rubidium, cesium, francium, beryllium, magnesium, calcium, strontium, barium, radium, zinc, chromium, samarium, and the like, as well as suitable combinations of any two or more thereof. Presently preferred reducing metals include lithium, sodium, potassium, magnesium, zinc, chromium, samarium, and the like, as well as suitable combinations of any two or more thereof.

Optionally, the combination utilized in accordance with this aspect of the present invention can further comprise a crown ether.

Typically, the components of the combination utilized in the aspect of the present invention directed to methods of reducing the chloride content of an epoxy compound starting material utilizing reducing metal(s) and nonhalogenated organic solvent(s) can be present in varying amounts.

The amount of epoxy compound starting material present in this combination is generally measured as a wt-wt % (compared to weight of the combination). Commonly, the combination utilized in the aspect of the present invention directed to methods of reducing the chloride content of an epoxy compound starting material utilizing reducing metal(s) and nonhalogenated organic solvent(s) comprises epoxy compound starting material in an amount from about 1 wt-wt % to about 50 wt-wt %, and preferably in an amount from about 10 wt-wt % to about 20 wt-wt %.

As readily recognized by those of skill in the art, the amount of reducing metal and nonhalogenated organic solvent present in this combination can be measured in a variety of ways (e.g., wt-wt % (compared to weight of the combination), mole equivalents when compared to epoxy starting compound, and the like). Thus, this combination comprises reducing metal in an amount from about 0.01 wt-wt % to about 20 wt-wt %, and preferably in an amount from about 0.05 wt-wt % to about 2 wt-wt %. Alternatively, this combination comprises reducing metal in an amount from about 1 to about 100 mole equivalents per mole equivalent of undesirable chloride content, and preferably in an amount from about 5 to about 20 mole equivalents per mole equivalent of undesirable chloride content. In addition, this combination comprises nonhalogenated organic solvent in an amount from about 50 wt-wt % to about 99 wt-wt %, and preferably in an amount from about 70 wt-wt % to about 90 wt-wt %. Alternatively, this combination comprises non-halogenated organic solvent in an amount from about 0.3 to about 500 mole equivalents per mole equivalent of epoxy starting compound, and preferably in an amount from about 5 to about 50 mole equivalents per mole of epoxy starting compound.

Without limiting this aspect of the invention in any way, this aspect of the invention is believed to give the lowest total chloride content of the different aspects of the invention methods. Thus, where a very low chloride content in the resulting treated epoxy compound is desired, this aspect of the invention methods would typically be utilized. However, since this aspect requires the use of reducing metals, this aspect may be somewhat less economical and more challenging to run than those aspects of the invention methods directed to crown ether/base or crown ether-like solvent/base treatment.

Optionally, the treated epoxy resin is more effectively separated from the combination by subjecting the combination and/or extracts from the combination to flash distillation (for small scale productions, utilizing, for example, a Kugelrohr distillation apparatus), or wiped fill still distillation (for large scale productions), or the like.

All percentages provided herein are weight/weight percentages. However, as recognized by those of skill in the art, the density between the epoxy compound starting materials and the treated epoxy compounds remain nearly constant during the treatment process, thereby permitting interchangeability of volume/volume percentages and weight/weight percentages.

All references cited herein are hereby incorporated herein by reference.

The invention will now be described in greater detail with reference to the following non-limiting examples. Those of ordinary skill in the art, when guided by the teachings of the specification, may discover during the term of this patent other embodiments of this invention which fall within the scope of the appended claims.

EXAMPLE 1

Exemplary Reduction of Chloride Content Utilizing Organic Solvent, Crown Ether, and Base A 1-liter round bottom flask equipped with a magnetic stirring bar and a water jacket was charged with toluene (500 ml) and a commercially available form of the diglycidyl ether of bisphenol A (100 g) (i.e., DER™ 332, commercially available from Dow Chemical Co., Midland, Mich., and having an EEW of 174, a total chloride content of 2026 ppm, and a hydrolyzable chloride content of 91 ppm). To the mixture was added 18-crown-6 (7.5 g) and a 50% by weight solution of potassium hydroxide in water (30.5 g). Stirring was commenced at which time the mixture was heated to reflux. A gentle reflux with stirring was maintained for 5 hours at which time the heating mantle was switched off and the reaction mixture was allowed to cool. The mixture was then poured into a 2-liter separatory funnel. The mixture (i.e., organic solution) was then washed three times with 500-ml portions of water. The organic layer of the washed mixture was then dried over magnesium sulfate, vacuum filtered, and concentrated in vacuo. The resulting oil was purified by bulb-to-bulb distillation under vacuum conditions (e.g., 0.4 mm Hg; 190° C. (oven)) over 25 min yielding 65.3 g of a colorless oil.

The colorless oil had an EEW of 173, a total chloride content of 523 ppm, and a hydrolyzable chloride content of <20 ppm.

EXAMPLE 2

Exemplary Reduction of Chloride Content Utilizing Crown Ether-Like Solvent and Base A 1-liter round bottom flask equipped with a magnetic stirring bar and a water jacket was charged with diglyme (500 ml) and a commercially available form of the diglycidyl ether of bisphenol A (100 g) (i.e., DER™ 332, commercially available from Dow Chemical Co., Midland, Mich., and having an EEW of 174, a total chloride content of 2026 ppm, and a hydrolyzable chloride content of 91 ppm). To the mixture was added a 50% by weight solution of potassium hydroxide in water (3.15 g). The flask was capped with a TEFLON™ stopper and stirring was initiated. The mixture was allowed to stir for 48 hours, at which time the magnetic stir bar was removed. The flask was connected to a rotary evaporator where 275 ml of the diglyme were removed by distillation at a bath temperature of 65° C. and pressure of 15 mm Hg. The remaining organic mixture was then poured into a 2-liter separatory funnel. To the mixture was added 500 ml methyl iso-butyl ketone (MIBK). The mixture (i.e., organic solution) was then washed three times with 500-ml portions of water. The organic layer of the washed mixture was then dried over magnesium sulfate, vacuum filtered, and concentrated in vacuo. The resulting oil was purified by bulb-to-bulb distillation under vacuum conditions (e.g., 0.4 mm Hg; 190° C. (oven)) over 25 min yielding 76.1 g of a colorless oil.

The colorless oil had an EEW of 170, and a total chloride content of 329 ppm.

EXAMPLE 3

Exemplary Reduction of Chloride Content Utilizing Aprotic Solvent and Hydride (Other than Tin Hydride)

A 1-liter round bottom flask equipped with a magnetic stirring bar and water jacketed condenser (which was also fitted with a rubber septum) was charged with tetrahydrofuran (500-ml) and a commercially available form of the diglycidyl ether of bisphenol A (100-g) (i.e., DER 332). Stirring was commenced at which time the reaction vessel was flushed with a steady stream of dry nitrogen for 20 min. To the mixture was added sodium hydride (4.17 g). The mixture was allowed to stir for an additional 3.5 hours at which time the remaining sodium hydride was quenched with 20 ml of water. The mixture was then poured into a 2-liter separatory funnel. To the mixture in the funnel was added hexane (350-ml) and diethyl ether (350-ml). The mixture (i.e., organic solution) was then washed three times with 500-ml portions of water. The organic layer of the washed mixture was then dried over magnesium sulfate, vacuum filtered, and concentrated in vacuo. The resulting oil was purified by bulb-to-bulb distillation under vacuum conditions (0.4 mm Hg; 190° C. (oven)) over 25 min yielding 92-g of a colorless oil.

The colorless oil had an EEW of 170, a total chloride content of 1083 ppm, and a hydrolyzable chloride content of <20 ppm.

EXAMPLE 4

Exemplary Reduction of Chloride Content Utilizing Nonhalogenated Organic Solvent and Reducing Metal A 1-liter three-neck round bottom flask equipped with a magnetic stirring bar, a rubber septum, a 500-ml pressure compensated additional funnel (which was fitted with a Teflon stopper and charged with 100 g of a commercially available form of the diglycidyl ether of bisphenol A (i.e., EPON® 825, commercially available from Shell Oil Company, Houston, Tex., and having an EEW of 172–178, a total chloride content of 1143 ppm, and a hydrolyzable chloride content of 39 ppm)) and water jacketed condenser (which was also fitted with a rubber septum) was charged with tetrahydrofuran (750 ml) and tert-butanol (1.9 ml). Stirring was commenced at which time the reaction vessel was flushed with a steady stream of dry nitrogen for 20 min. The mixture in the flask was heated to reflux at which time fine strips (approximate 10 mm×25 mm×1 mm) of sodium metal (1.32 g) were added. Subsequently, the diglycidyl ether of bisphenol A in the addition funnel was slowly added to the mixture in the flask over 2 h. The mixture was held at reflux with continued stirring for the next 2 days at which time the mixture was allowed to cool to 25° C. The remaining sodium metal in the mixture was quenched with methanol (100-ml). The mixture was then poured into a 2-liter separatory funnel. To the mixture in the funnel was added hexane (500-ml) and diethyl ether (500-ml). The resulting organic solution was then washed three times with 600 ml portions of water. The organic layer of the washed organic solution was then dried over magnesium sulfate, vacuum filtered, and concentrated in vacuo. The resulting oil was purified by bulb-to-bulb distillation under vacuum conditions (e.g., 0.4 mm Hg; 190° C. (oven)) over 25 min yielding 83.4 g of colorless oil.

The colorless oil had an EEW of 172, a total chloride content of 166 ppm, and a hydrolyzable chloride content of <20 ppm.

EXAMPLE 5

Exemplary Reduction of Chloride Content Utilizing Nonhalogenated Organic Solvent, Reducing Metal and Crown Ether A 1-liter round bottom flask equipped with a magnetic stirring bar and a rubber septum was charged with toluene (500-ml), 18-crown-6 (7.46 g) and a commercially available form of the diglycidyl ether of bisphenol A (100-g) (i.e., DER 332). Stirring was commenced at which time the reaction vessel was flushed with a steady stream of dry nitrogen for 20 min. To the mixture in the flask was added finely sliced slices (approximately 1 mm thick and 20 mm in diameter) of potassium metal (1.10 g). The mixture in the flask was allowed to stir for an additional 4 hours at which time the remaining potassium in the flask was quenched with ethanol (40-ml), the mixture was then poured into a 2-liter separatory funnel. The mixture (i.e., organic mixture) was then washed three times with 500-ml portions of water. The organic layer of the washed organic mixture was then dried over magnesium sulfate, vacuum filtered, and concentrated in vacuo. The resulting oil was purified by bulb-to-bulb distillation under vacuum [0.4 Hg, 190° C. (oven)] over 25 min yielding 90.3-g of a colorless oil.

The colorless oil had an EEW of 177, a total chloride content of 824 ppm, and a hydrolyzable chloride content of <20 ppm.

While the invention has been described in detail with reference to certain preferred embodiments thereof, it will be understood that modifications and variations are within the spirit and scope of that which is described and claimed.

That which is claimed is:

1. A method of reducing the chloride content of an epoxy compound starting material, said method comprising:
   a) subjecting a combination comprising said epoxy compound starting material, an organic solvent, a crown ether, and a suitable base to conditions sufficient to produce a treated epoxy compound, wherein the chloride content of said treated epoxy compound is reduced by at least a predetermined value, relative to the chloride content of said epoxy compound starting material, and
   b) separating said treated epoxy compound from said combination.

2. A method according to claim 1, wherein the predetermined value by which said chloride content is reduced is 50% of the chloride content of said epoxy compound starting material.

3. A method according to claim 1, wherein the predetermined value by which said chloride content is reduced is 70% of the chloride content of said epoxy compound starting material.

4. A method according to claim 1, wherein the predetermined value by which said chloride content is reduced is 90% of the chloride content of said epoxy compound starting material.

5. A method according to claim 1, wherein said conditions sufficient to produce said treated epoxy compound comprise subjecting said combination to a temperature from about −78° C. to about 250° C.

6. A method according to claim 1, wherein said conditions sufficient to produce said treated epoxy compound comprise subjecting said combination to a temperature from about 10° C. to about 150° C.

7. A method according to claim 1, wherein said conditions sufficient to produce said treated epoxy compound comprise subjecting said combination to a temperature from about 25° C. to about 120° C.

8. A method according to claim 1, wherein said treated epoxy compound is produced by subjecting said combination to a pressure from about 5 torr to about 300,000 torr.

9. A method according to claim 1, wherein said treated epoxy compound is produced by subjecting said combination to a pressure from about 400 torr to about 1,000 torr.

10. A method according to claim 1, wherein said combination is subjected to said conditions sufficient to produce said treated epoxy compound starting material for about 0.1 to about 168 hours.

11. A method according to claim 1, wherein said combination is subjected to conditions sufficient to produce said treated epoxy compound starting material for about 1 to about 24 hours.

12. A method according to claim 1, wherein said epoxy compound starting material is a glycidyl ether of a phenol, a cresol formaldehyde, a polyhydroxy phenol, a polyaromatic phenol, an aliphatic alcohol, a polyglycol, an aromatic amine, or a combination of any two or more thereof.

13. A method according to claim 1, wherein said epoxy compound starting material is:
   a glycidyl ether of a phenol selected from a phenyl glycidyl ether, a cresyl glycidyl ether, a nonylphenyl glycidyl ether, or a p-tert-butylphenyl glycidyl ether,
   a diglycidyl ether of a bisphenol selected from bisphenol A, bisphenol F, ethylidinebisphenol, dihydroxydiphenyl ether, N,N'-disalicylal-ethylenediamine, arin, bis(4-hydroxyphenyl)sulfone, bis(hydroxyphenyl)sulfide, 1,1 -bis(hydroxyphenyl)cyclohexane, 9,19-bis(4-hydroxyphenyl)fluorene, 1,1,1-tris(hydroxyphenyl) ethane, trihydroxytritylmethane, 4,4'-(1-alpha-methylbenzylidene)bisphenol, 4,4'-(1,3-diethylethylene)diphenol, diethylstilbesterol, 4,4'-dihyroxybenzophenone, resorcinol, catechol, or tetrahydroxydiphenyl sulfide
   a glycidyl ether of a cresol formaldehyde,
   a glycidyl ether of a fused ring polyaromatic phenol selected from dihydroxy naphthalene, 2,2'-dihydroxy-6,6'-dinaphthyl disulfide, or 1,8,9-trihydroxyanthracene
   a glycidyl ether of an aliphatic alcohol selected from a diglycidyl ether of 1,4 butanediol, a diglycidyl ether of neopentyl glycol, a diglycidyl ether of cyclohexane dimethanol, a trimethyol ethane triglycidyl ether, or a trimethyol propane triglycidyl ether,
   a glycidyl ether of a polyglycol selected from Heloxy 84™, Heloxy 32™, a polyglycidyl ether of castor oil, or a polyoxypropylene diglycidyl ether,
   a glycidyl ether of an aromatic amine, or
   a combination of any two or more thereof.

14. A method according to claim 1, wherein said organic solvent is a halogenated solvent, hydrocarbon solvent, aromatic hydrocarbon solvent, ether solvent, cyclic ether solvent, alcohol solvent, glycol solvent, alcohol ether solvent, ketone solvent, nitrile solvent, sulfoxide solvent, or amide solvent, or a combination of any two or more thereof.

15. A method according to claim 1, wherein said organic solvent is carbon tetrachloride, methylene chloride, chloroform, tetrachloroethylene, chlorobenzene, bis(2-chloroethyl)ether, chloromethyl ethyl ether, chloromethyl methyl ether, 2-chloroethyl ethyl ether, 2-chloroethyl propyl ether, 2-chloroethyl methyl ether, pentane, hexane, cyclohexane, heptane, octane, decahydronaphthalene, petroleum ethers, ligroine, benzene, naphthalene, toluene, xylene, ethyl benzene, cumene (iso-propyl benzene)mesitylene (trimethyl benzene), ethyl toluene, butyl benzene, cymene (iso-propyl toluene), diethylbenzene, iso-butyl benzene, tetramethyl benzene, sec-butyl benzene, tert-butyl benzene, diethyl ether, ethyl propyl ether, dipropyl ether, diisopropyl ether, dibutyl ether, methyl t-butyl ether, glyme, diglyme, benzyl methyl ether, isochroman, 2-phenylethyl methyl ether, n-butyl ethyl ether, 1,2-diethoxyethane, sec-butyl ether, diisobutyl ether, ethyl n-propyl ether, ethyl isopropyl ether, n-hexyl methyl ether, n-butyl methyl ether, methyl n-propyl ether, tetrahydrofuran, dioxane, tetrahydropyran, 4 methyl-1,3-dioxane, 4-phenyl-1,3-dioxane, 1,3-dioxolane, 2-methyl-1,3-dioxolane, 1,4-dioxane, 1,3-dioxane, 2,5-dimethoxytetrahydrofuran, 2,5-dimethoxy-2,5-dihydrofuran, methanol, ethanol, 1-propanol, 2-propanol, 1-butanol, 2-butanol, 2-methyl-1-propanol, 2-methyl-2-propanol, 1-pentanol, 2-pentanol, 3-pentanol, 2,2-dimethyl-1-propanol, 1-hexanol, cyclopentanol, 3-methyl-1-butanol, 3-methyl-2-butanol, 2-methyl-1-butanol, 2,2-dimethyl-1-propanol, 3-hexanol, 2-hexanol, 4-methyl-2-pentanol, 2-methyl-1-pentanol, 2-ethylbutanol, 2,4-dimethyl-3-pentanol, 3-heptanol, 4-heptanol, 2-heptanol, 1-heptanol, 2-ethyl-1-hexanol, 2,6-dimethyl-4-heptanol, 2-methylcyclohexanol, 3-methylcyclohexanol, 4-methylcyclohexanol, ethylene glycol, 1,3-propanediol, 1,2-propanediol, 1,3-butanediol, 1,4-butanediol, 2,3-butanediol, 3-methyl-1,5-pentanediol, 1,4-cyclohexanediol, 1,3-cyclohexanediol, 1,4-cyclohexanedimethanol, dipropylene glycol, 1-methoxy-2-propanol, 2-methoxyethanol, 2-ethoxyethanol, 1-methoxy-2-butanol, ethylene glycol monoisopropyl ether, 1-ethoxy-2-propanol, 3-methoxy-1-butanol, ethylene glycol monoisobutyl ether, ethylene glycol mono-n-butyl ether, 3-methoxy-3-methylbutanol, ethylene glycol momo-tert-butyl ether, acetone, methylethyl ketone, methyl iso-butyl ketone, cyclohexanone, isopropyl methyl ketone, 2-pentanone, 3-pentanone, 3-hexanone, diisopropyl ketone, 2-hexanone, cyclopentanone, 4-heptanone, iso-amyl methyl ketone, 3-heptanone, 2-heptanone, 4-methoxy-4-methyl-2-pentanone, 5-methyl-3-heptanone, 2-methylcyclohexanone, diisobutyl ketone, 5-methyl-2-octanone, 3-methylcyclohexanone, 2-cyclohexen-1-one, 4-methylcyclohexanone, cycloheptanone, 4-tert-butylcyclohexanone, isophorone, benzyl acetone, acetonitrile, acrylonitrile, trichloroacetonitrile, propionitrile, pivalonitrile, isobutyronitrile, n-butyronitrile, methoxyacetonitrile, 2-methylbutyronitrile, isovaleronitrile, N-valeronitrile, n-capronitrile, 3 -methoxypropionitrile, 3-ethoxypropionitrile, 3,3'-oxydipropionitrile, n-heptanenitrile, glycolonitrile, benzonitrile, ethylene cyanohydrin, succinonitrile, acetone cyanohydrin, 3-n-butoxypropionitrile, dimethyl sulfoxide, di-n-butyl sulfoxide, tetramethylene sulfoxide, methyl phenyl sulfoxide, dimethyl formamide, dimethyl acetamide, acylamide, 2-acetamidoethanol, N,N-dimethyl-m-toluamide, trifluoroacetamide, N,N-dimethylacetamide, N,N-diethyldodecanamide, epsilon-caprolactam, N,N-diethylacetamide, N-tert-butylformamide, formamide, pivalamide, N-butyramide, N,N-dimethlacetoacetamide, N-methyl formamide, N,N-diethylformamide, N-formylethylamine, acetamide, N,N-diisopropylformamide, 1-formylpiperidine, N-methylformanilide, or a combination of any two or more thereof.

16. A method according to claim 1, wherein said crown ether is benzo-15-crown-5; benzo-18-crown-6; 12-crown-4; 15-crown-5; 18-crown-6; cyclohexano-15-crown-5; 4',4"(5")-ditert-butyldibenzo-18-crown-6; 4',4"(5")-ditert-butyldicyclohexano-18-crown-6; dicyclohexano-18-crown-6; dicyclohexano-24-crown-8; 4'-aminobenzo-15-crown-5; 4'-aminobenzo-18-crown-6; 2-(aminomethyl)-15-crown-5; 2-(aminomethyl)-18-crown-6; 4'-amino-5'-nitrobenzo-15-crown-5; 1-aza-12-crown-4; 1-aza-15-crown-5; 1-aza-18-crown-6; benzo-12-crown-4; benzo-15-crown-5; benzo-18-crown-6; bis((benzo-15-crown-5)-15-ylmethyl)pimelate; 4-bromobenzo-18-crown-6; (+)-(18-crown-6)-2,3,11,12-tetra-carboxylic acid; dibenzo-18-crown-6; dibenzo-24-crown-8; dibenzo-30-crown-10; ar-ar'-di-tert-butyldibenzo-18-crown-6; 4'-formylbenzo-15-crown-5; 2-(hydroxymethyl)-12-crown-4; 2-(hydroxymethyl)-15-crown-5; 2-(hydroxymethyl)-18-crown-6; 4'-nitrobenzo-15-crown-5; poly-[(dibenzo-18-crown-6)-co-formaldehyde]; 1,1-dimethylsila-11-crown-4; 1,1-dimethylsila-14-crown-5; 1,1-dimethylsila-17-crown-5; cyclam; 1,4,10,13-tetrathia-7, 16-diazacyclooctadecane; a porphine, or a combination of any two or more thereof.

17. A method according to claim 1, wherein said base is an alkoxide or hydroxide, a carbonate, a bicarbonate, a phosphate, or combination of any two or more thereof.

18. A method according to claim 17, wherein said alkoxide or hydroxide is sodium hydroxide, potassium hydroxide, lithium hydroxide, rubidium hydroxide, cesium hydroxide, francium hydroxide, beryllium hydroxide, magnesium hydroxide, calcium hydroxide, strontium hydroxide, barium hydroxide, radium hydroxide, lithium methoxide, lithium ethoxide, lithium propoxide, lithium iso-propoxide, lithium butoxide, lithium iso-butoxide, lithium sec-butoxide, lithium tert-butoxide, sodium methoxide, sodium ethoxide, sodium propoxide, sodium iso-propoxide, sodium butoxide, sodium iso-butoxide, sodium sec-butoxide, sodium tert-butoxide, potassium methoxide, potassium ethoxide, potassium propoxide, potassium iso-propoxide, potassium butoxide, potassium iso-butoxide, potassium sec-butoxide, potassium tert-butoxide, lithium carbonate, lithium bicarbonate, sodium carbonate, sodium bicarbonate, potassium carbonate, potassium bicarbonate, or a combination of any two or more thereof.

19. A method according to claim 17, wherein said carbonate is sodium hydrogen carbonate, potassium hydrogen carbonate, lithium carbonate, or a combination of any two or more thereof.

20. A method according to claim 17, wherein said bicarbonate is sodium bicarbonate, potassium bicarbonate, lithium bicarbonate, cesium bicarbonate, ammonium bicarbonate, or a combination of any two or more thereof.

21. A method according to claim 17, wherein said phosphate is sodium phosphate, potassium phosphate, lithium phosphate, ammonium phosphate, or a combination of any two or more thereof.

22. A method according to claim 1, wherein said combination comprises about 1 wt-wt % to about 75 wt-wt % of said epoxy compound starting material, about 25 wt-wt % to about 98 wt-wt % of said organic solvent, about 0.00001 wt-wt % to about 20 wt-wt % of said crown ether, and about 0.01 wt-wt % to about 10 wt-wt % of said base.

23. A method according to claim 1, wherein said combination comprises about 1 wt-wt % to about 75 wt-wt % of said epoxy compound starting material, about 25 wt-wt % to about 98 wt-wt % of said organic solvent, about 0.1 to about 20 mole equivalents of said crown ether per mole equivalent of undesirable chloride content, and about 0.1 to about 20 mole equivalents of said base per mole equivalent of undesirable chloride content.

24. A method according to claim 1, wherein said combination comprises about 10 wt-wt % to about 30 wt-wt % of said epoxy compound starting material, about 70 wt-wt % to about 90 wt-wt % of said organic solvent, about 1 to about 5 mole equivalents of said crown ether per mole equivalent of undesirable chloride content, and about 1 to about 5 mole equivalents of said base per mole equivalent of undesirable chloride content.

25. A method of reducing the chloride content of an epoxy compound starting material, said method comprising:
   a) subjecting a combination comprising said epoxy compound starting material, a crown ether-like solvent, and a suitable base to conditions sufficient to produce a treated epoxy compound, wherein the chloride content of said treated epoxy compound is reduced by at least a predetermined value, relative to the chloride content of said epoxy compound starting material, and
   b) separating said treated epoxy compound from said combination.

26. A method according to claim 25, wherein said treated epoxy compound is produced by subjecting said combination to a pressure from about 5 torr to about 300,000 torr.

27. A method according to claim 25, wherein said crown ether-like solvent is 1,2-dimethoxy ethane, bis(2-methoxyethyl)ether, 1,2-diethoxyethane, 1,2-bis(2-methoxyethoxy)ethane, 2-(2-methoxyethoxy)ethanol, Bis (2-ethoxyethyl)ether, polyethylene glycols having an average molecular weight in the range from about 200 to about 10,000, or a combination of any two or more thereof.

28. A method according to claim 25, wherein said combination comprises about 1 wt-wt % to about 75 wt-wt % of said epoxy compound starting material, about 25 wt-wt % to about 98 wt-wt % of said crown ether-like solvent, and about 0.01 wt-wt % to about 10 wt-wt % of said base.

29. A method according to claim 25, wherein said combination comprises about 10 wt-wt % to about 30 wt-wt % of said epoxy compound starting material, about 70 wt-wt % to about 90 wt-wt % of said crown ether-like solvent, and about 0.1 to about 20 mole equivalents of said base per mole equivalent of undesirable chloride content.

30. A method according to claim 25, wherein said combination comprises about 10 wt-wt % to about 30 wt-wt % of said epoxy compound starting material, about 70 wt-wt % to about 90 wt-wt % of said crown ether-like solvent, and about 1 to about 5 equivalents of said base per mole equivalent of undesirable chloride content.

31. A method of reducing the chloride content of an epoxy compound starting material, said method comprising:
   a) subjecting a combination comprising said epoxy compound starting material, an aprotic solvent, and a hydride other than tin hydride to conditions sufficient to produce a treated epoxy compound, wherein the chloride content of said treated epoxy compound is reduced by at least a predetermined value, relative to the chloride content of said epoxy compound starting material, and
   b) separating said treated epoxy compound from said combination.

32. A method according to claim 31, wherein said treated epoxy compound starting material is produced by subjecting said combination to a pressure from about 5 torr to about 300,000 torr.

33. A method according to claim 31, wherein said aprotic solvent is a halogenated solvent, hydrocarbon solvent, aromatic hydrocarbon solvent, ether solvent, cyclic ether solvent, ketone solvent, nitrile solvent, sulfoxide solvent, amide solvent, or a combination of any two or more thereof.

34. A method according to claim 33, wherein said aprotic solvent is carbon tetrachloride, methylene chloride, chloroform, tetrachloroethylene, chlorobenzene, bis(2-chloroethyl)ether, chloromethyl ethyl ether, chloromethyl methyl ether, 2-chloroethyl ethyl ether, 2-chloroethyl propyl ether, 2-chloroethyl methyl ether, pentane, hexane, cyclohexane, heptane, octane, decahydronaphthalene, petroleum ethers, ligroine, benzene, naphthalene, toluene, xylene, ethyl benzene, cumene (iso-propyl benzene)mesitylene (trimethyl benzene), ethyl toluene, butyl benzene, cymene (iso-propyl toluene), diethylbenzene, iso-butyl benzene, tetramethyl benzene, sec-butyl benzene, tert-butyl benzene, diethyl ether, ethyl propyl ether, dipropyl ether, diisopropyl ether, dibutyl ether, methyl t-butyl ether, glyme, diglyme, benzyl methyl ether, isochroman, 2-phenylethyl methyl ether, n-butyl ethyl ether, 1,2-diethoxyethane, sec-butyl ether, diisobutyl ether, ethyl n-propyl ether, ethyl isopropyl ether, n-hexyl methyl ether, n-butyl methyl ether, methyl n-propyl ether, tetrahydrofuran, dioxane, tetrahydropyran, 4 methyl-1,3-dioxane, 4-phenyl-1,3-dioxane, 1,3-dioxolane, 2-methyl-1,3-dioxolane, 1,4-dioxane, 1,3-dioxane, 2,5-dimethoxytetrahydrofuran, 2,5-dimethoxy-2,5- dihydrofuran, acetone, methylethyl ketone, methyl iso-butyl ketone, cyclohexanone, isopropyl methyl ketone, 2-pentanone, 3-pentanone, 3-hexanone, diisopropyl ketone, 2-hexanone, cyclopentanone, 4-heptanone, iso-amyl methyl ketone, 3-heptanone, 2-heptanone, 4-methoxy-4-methyl-2-pentanone, 5-methyl-3-heptanone, 2-methylcyclohexanone, diisobutyl ketone, 5-methyl-2-octanone, 3-methylcyclohexanone, 2-cyclohexen-1-one, 4-methylcyclohexanone, cycloheptanone, 4-tert-butylcyclohexanone, isophorone, benzyl acetone, acetonitrile, acrylonitrile, trichloroacetonitrile, propionitrile, pivalonitrile, isobutyronitrile, n-butyronitrile, methoxyacetonitrile, 2-methylbutyronitrile, isovaleronitrile, N-valeronitrile, n-capronitrile, 3-methoxypropionitrile, 3-ethoxypropionitrile, 3,3'-oxydipropionitrile, n-heptanenitrile, glycolonitrile, benzonitrile, ethylene cyanohydrin, succinonitrile, acetone cyanohydrin, 3-n-butoxypropionitrile, dimethyl sulfoxide, di-n-butyl sulfoxide, tetramethylene sulfoxide, methyl phenyl sulfoxide, dimethyl formamide, dimethyl acetamide, acylamide, 2-acetamidoethanol, N,N-dimethyl-m-toluamide, trifluoroacetamide, N,N-dimethylacetamide, N,N-diethyldodecanamide, epsilon-caprolactam, N,N-diethylacetamide, N-tert-butylformamide, formamide, pivalamide, N-butyramide, N,N-dimethlacetoacetamide, N-methyl formamide, N,N-diethylformamide, N-formylethylamine, acetamide, N,N-diisopropylformamide, 1-formylpiperidine, N-methylformanilide, or a combination of any two or more thereof.

35. A method according to claim 31, wherein said hydride is a metal hydride from the Group 1 elements, a metal hydride from the Group 2 elements, or a combination of any two or more thereof.

36. A method according to claim 31, wherein said hydride is lithium hydride, sodium hydride, potassium hydride, rubidium hydride, cesium hydride, francium hydride, beryllium hydride, magnesium hydride, calcium hydride, strontium hydride, barium hydride, radium hydride, or a combination of any two or more thereof.

37. A method according to claim 31, wherein said combination comprises about 1 wt-wt % to about 70 wt-wt % of said epoxy compound starting material, about 30 wt-wt % to about 99 wt-wt % of said aprotic solvent, and about 0.00001 wt-wt % to about 20 wt-wt % of said hydride.

38. A method according to claim 31, wherein said combination comprises about 1 wt-wt % to about 70 wt-wt % of said epoxy compound starting material, about 30 wt-wt % to about 99 wt-wt % of said aprotic solvent, and about 0.1 to about 25 mole equivalent of said hydride per mole equivalent of undesirable chloride content.

39. A method according to claim 31, wherein said combination comprises about 10 wt-wt % to about 30 wt-wt % of said epoxy compound starting material, about 70 wt-wt % to about 90 wt-wt % of said aprotic solvent, and about 1 wt-wt % to about 10 wt-wt % of said hydride.

40. A method according to claim 31, wherein said combination comprises about 10 wt-wt % to about 30 wt-wt % of said epoxy compound starting material, about 70 wt-wt % to about 90 wt-wt % of said aprotic solvent, and about 1 to about 5 mole equivalent of said hydride per mole equivalent of undesirable chloride content.

41. A method according to claim 31, wherein said conditions sufficient to reduce the chloride content of said epoxy compound of step (a) comprise heating and stirring the combination at a predetermined elevated temperature for a predetermined time sufficient to produce said treated epoxy compound.

42. A method according to claim 31, wherein said separation of step (b) is accomplished by biphasic extraction, dual distillation or chromatography.

43. A method of reducing the chloride content of an epoxy compound starting material, said method comprising:
  a) subjecting a combination comprising said epoxy compound starting material, an organic solvent, and a reducing metal to conditions sufficient to produce a treated epoxy compound, wherein the chloride content of said treated epoxy compound is reduced by at least a predetermined value, relative to the chloride content of said epoxy compound starting material; and
  b) separating said treated epoxy compound from said combination.

44. A method according to claim 43, wherein said treated epoxy compound starting material is produced by subjecting said combination to a pressure from about torr to about 300,000 torr.

45. A method according to claim 43, wherein said organic solvent is a hydrocarbon solvent, aromatic hydrocarbon solvent, ether solvent, cyclic ether solvent, alcohol solvent, ketone solvent, nitrile solvent, sulfoxide solvent, amide solvent, or a combination of any two or more thereof.

46. A method according to claim 43, wherein said organic solvent is pentane, hexane, cyclohexane, heptane, octane, decahydronaphthalene, petroleum ethers, ligroine, benzene, naphthalene, toluene, xylene, ethyl benzene, cumene (isopropyl benzene)mesitylene (trimethyl benzene), ethyl toluene, butyl benzene, cymene (iso-propyl toluene), diethylbenzene, iso-butyl benzene, tetramethyl benzene, sec-butyl benzene, tert-butyl benzene, diethyl ether, ethyl propyl ether, dipropyl ether, diisopropyl ether, dibutyl ether, methyl t-butyl ether, glyme, diglyme, benzyl methyl ether, isochroman, 2-phenylethyl methyl ether, n-butyl ethyl ether, 1,2-diethoxyethane, sec-butyl ether, diisobutyl ether, ethyl n-propyl ether, ethyl isopropyl ether, n-hexyl methyl ether, n-butyl methyl ether, methyl n-propyl ether, tetrahydrofuran, dioxane, tetrahydropyran, 4 methyl-1,3-dioxane, 4-phenyl-1,3-dioxane, 1,3-dioxolane, 2-methyl-1,3-dioxolane, 1,4-dioxane, 1,3-dioxane, 2,5-dimethoxytetrahydrofuran, 2,5-dimethoxy-2,5-dihydrofuran, methanol, ethanol, 1-propanol, 2-propanol, 1-butanol, 2-butanol, 2-methyl-1-propanol, 2-methyl-2-propanol, 1-pentanol, 2-pentanol, 3-pentanol, 2,2-dimethyl-1-propanol, 1-hexanol, cyclopentanol, 3-methyl-1-butanol, 3-methyl-2-butanol, 2-methyl-1-butanol, 2,2-dimethyl-1-propanol, 3-hexanol, 2-hexanol, 4-methyl-2-pentanol, 2-methyl-1-pentanol, 2-ethylbutanol, 2,4-dimethyl-3-pentanol, 3-heptanol, 4-heptanol, 2-heptanol, 1-heptanol, 2-ethyl-1-hexanol, 2,6-dimethyl-4-heptanol, 2-methylcyclohexanol, 3-methylcyclohexanol, 4-methylcyclohexanol, ethylene glycol, 1,3-propanediol, 1,2-propanediol, 1,3-butanediol, 1,4-butanediol, 2,3-butanediol, 3-methyl-1,5-pentanediol, 1,4-cyclohexanediol, 1,3-cyclohexanediol, 1,4-cyclohexanedimethanol, dipropylene glycol, 1-methoxy-2-propanol, 2-methoxyethanol, 2-ethoxyethanol, 1-methoxy-2-butanol, ethylene glycol monoisopropyl ether, 1-ethoxy-2-propanol, 3-methoxy-1-butanol, ethylene glycol monoisobutyl ether, ethylene glycol mono-n-butyl ether, 3-methoxy-3-methylbutanol, ethylene glycol momo-tert-butyl ether, acetone, methylethyl ketone, methyl iso-butyl ketone, cyclohexanone, isopropyl methyl ketone, 2-pentanone, 3-pentanone, 3-hexanone, diisopropyl ketone, 2-hexanone, cyclopentanone, 4-heptanone, iso-amyl methyl ketone, 3-heptanone, 2-heptanone, 4-methoxy-4-methyl-2-pentanone, 5-methyl-3-heptanone, 2-methylcyclohexanone, diisobutyl ketone, 5-methyl-2-octanone, 3-methylcyclohexanone, 2-cyclohexen-1-one, 4-methylcyclohexanone, cycloheptanone, 4-tert-butylcyclohexanone, isophorone, benzyl acetone, acetonitrile, acrylonitrile, trichloroacetonitrile, propionitrile, pivalonitrile, isobutyronitrile, n-butyronitrile, methoxyacetonitrile, 2-methylbutyronitrile, isovaleronitrile, N-valeronitrile, n-capronitrile, 3-methoxypropionitrile, 3-ethoxypropionitrile, 3,3'-oxydipropionitrile, n-heptanenitrile, glycolonitrile, benzonitrile, ethylene cyanohydrin, succinonitrile, acetone cyanohydrin, 3-n-butoxypropionitrile, dimethyl sulfoxide, di-n-butyl sulfoxide, tetramethylene sulfoxide, methyl phenyl sulfoxide, dimethyl formamide, dimethyl acetamide, acylamide, 2-acetamidoethanol, N,N-dimethyl-m-toluamide, trifluoroacetamide, N,N-dimethylacetamide, N,N-diethyldodecanamide, epsilon-caprolactam, N,N-diethylacetamide, N-tert-butylformamide, formamide, pivalamide, N-butyramide, N,N-dimethlacetoacetamide, N-methyl formamide, N,N-diethylformamide, N-formylethylamine, acetamide, N,N-diisopropylformamide, 1-formylpiperidine, N-methylformanilide, or a combination of any two or more thereof.

47. A method according to claim 43, wherein said reducing metal is a Group 1 metal, Group 2 metal, transition metal, lanthanide, actinide, or a combination of any two or more thereof.

48. A method according to claim 43, wherein said reducing metal is lithium, sodium, potassium, rubidium, cesium, francium, beryllium, magnesium, calcium, strontium, barium, radium, zinc, chromium, samarium, or a combination of any two or more thereof.

49. A method according to claim 43, wherein said reducing metal is lithium, sodium, potassium, magnesium, zinc, chromium, samarium, or a combination of any two or more thereof.

50. A method according to claim 43, wherein said combination further comprises a crown ether.

51. A method according to claim 43, wherein said crown ether is benzo-15-crown-5; benzo-18-crown-6; 12-crown-4; 15-crown-5; 18-crown-6; cyclohexano-15-crown-5; 4',4"(5")-ditert-butyldibenzo-18-crown-6; 4',4"(5")-ditert-butyldicyclohexano-18-crown-6; dicyclohexano-18-crown-6; dicyclohexano-24-crown-8; 4'-aminobenzo-15-crown-5; 4'-aminobenzo-18-crown-6; 2-(aminomethyl)-15-crown-5; 2-(aminomethyl)-18-crown-6; 4'-amino-5 '-nitrobenzo-15-crown-5; 1-aza-12-crown-4; 1-aza-15-crown-5; 1-aza-18-crown-6; benzo-1 2-crown-4; benzo-15-crown-5; benzo-18-crown-6; bis((benzo-15-crown-5)-15-ylmethyl)pimelate; 4-bromobenzo-18-crown-6; (+)-(18-crown-6)-2,3,11,12-tetra-carboxylic acid; dibenzo-18-crown-6; dibenzo-24-crown-8; dibenzo-30-crown-10; ar-ar'-di-tert-butyldibenzo-18-crown-6; 4'-formylbenzo-15-crown-5; 2-(hydroxymethyl)-12-crown-4; 2-(hydroxymethyl)-15-crown-5; 2-(hydroxymethyl)-18-crown-6; 4'-nitrobenzo-15-crown-5; poly-[(dibenzo-18-crown-6)-co-formaldehyde]; 1,1-dimethylsila-11-crown-4; 1,1-dimethylsila-14-crown-5; 1,1-dimethylsila-17-crown-5; cyclam; 1,4,10,13-tetrathia-7,16-diazacyclooctadecane; porphines; or a combination of any two or more thereof.

* * * * *

UNITED STATES PATENT AND TRADEMARK OFFICE
CERTIFICATE OF CORRECTION

PATENT NO.   : 6,211,389 B1
DATED        : April 3, 2001
INVENTOR(S)  : Dimke

It is certified that error appears in the above-identified patent and that said Letters Patent is hereby corrected as shown below:

<u>Column 28,</u>
Line 17, after "from about" and before "torr" insert -- 5 --.

Signed and Sealed this

Twelfth Day of November, 2002

Attest:

Attesting Officer

JAMES E. ROGAN
Director of the United States Patent and Trademark Office